United States Patent [19]

Nakamura et al.

[11] Patent Number: 4,469,899

[45] Date of Patent: Sep. 4, 1984

[54] PROCESS FOR PRODUCING PHLOROGLUCIN

[75] Inventors: Makoto Nakamura, Ibaraki; Tsutomu Chiyoda, Toyonaka; Shinichi Hasegawa, Otsu, all of Japan

[73] Assignee: Sumitomo Chemical Company, Limited, Osaka, Japan

[21] Appl. No.: 407,159

[22] Filed: Aug. 11, 1982

[30] Foreign Application Priority Data

Aug. 27, 1981 [JP] Japan ................................. 56-134894

[51] Int. Cl.$^3$ ...................... C07C 37/08; C07C 39/12
[52] U.S. Cl. .................................... 568/768; 568/771; 568/798; 568/803; 568/763
[58] Field of Search .............. 568/798, 803, 763, 771, 568/768

[56] References Cited

U.S. PATENT DOCUMENTS 2,790,010  4/1957  Shepard ............................. 568/768
4,267,387  5/1981  Imai et al. ......................... 568/568
4,334,108  6/1982  Hashimoto et al. ............... 568/803

FOREIGN PATENT DOCUMENTS 12239  10/1956  German Democratic Rep. .................................. 568/768
751598  6/1956  United Kingdom ............... 568/768

*Primary Examiner*—Werren B. Lone
*Attorney, Agent, or Firm*—Stevens, Davis, Miller & Mosher

[57] ABSTRACT

A process for producing phloroglucin important as an intermediate compound of medicine, sensitizer and the like which comprises reacting an oxidation product containing at least one carbinol compound of carbinol dihydroperoxide, dicarbinol hydroperoxide and tricarbinol obtained by oxidation of 1,3,5-triisopropylbenzene, with hydrogen peroxide in a heterogeneous system in the presence of an acid catalyst and an organic solvent inert to the hydrogen peroxide and capable of dissolving the oxidation product, and decomposing the reaction product with an acid.

3 Claims, No Drawings

PROCESS FOR PRODUCING PHLOROGLUCIN

This invention relates to a process for producing phloroglucin important as an intermediate for sensitizers and medicines, in high yields, which comprises reacting hydrogen peroxide with a product containing at least one carbinol compound of carbinol dihydroperoxide, dicarbinol hydroperoxide, and tricarbinol obtained by oxidation of 1,3,5-triisopropylbenzene, in a heterogeneous system in the presence of an acid catalyst and an organic solvent inert to hydrogen peroxide and capable of dissolving the oxidation product, and decomposing the reaction product with an acid.

It is described in D.D. Pat. No. 12239 and U.S Pat. No. 2,790,010 that phloroglucin is produced by oxidizing 1,3,5-triisopropylbenzene (hereinafter referred to as TIPB) into 1,3,5-triisopropylbenzene trihydroperoxide (hereinafter referred to as THPO), represented by the formula,

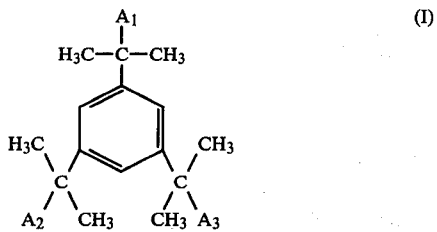

wherein $A_1$, $A_2$ and $A_3$ all represent —OOH, and decomposing THPO with an acid. In these patent specifications, however, there is no recognition concerning carbinol compounds incidentally produced by the oxidation of TIPB which are represented by the above formula (I) and include carbinol dihydroperoxide ($A_1$:—OH; $A_2$ and $A_3$:—OOH), dicarbinol hydroperoxide ($A_1$ and $A_2$:—OH; $A_3$:—OOH), and tricarbinol ($A_1$, $A_2$ and $A_3$:—OH) (hereinafter, the term "carbinol compounds" means these compounds); the described processes comprise decomposing the oxidation product of TIPB as it is or decomposing THPO isolated from the oxidation product, in the presence of an acid; and the yield of phloroglucin based on the starting material TIPB is extremely low.

Noting these carbinol compounds, the present inventors studied the production of phloroglucin, and as a result confirmed that, on decomposition with an acid, these carbinol compounds themselves do not give phloroglucin, and THPO containing them, gives a lower yield of phloroglucin than does THPO not containing them.

In view of the above, the present inventors further investigated processes for producing phloroglucin from carbinol compound-containing products obtained by oxidation of TIPB, in order to obtain phloroglucin in a high yield. Thus, this invention has been accomplished.

This invention provides a process for producing phloroglucin comprising reacting hydrogen peroxide with a product, containing at least one carbinol compound, obtained by oxidation of TIPB, in a heterogeneous system in the presence of an acid catalyst and an organic solvent inert to hydrogen peroxide and capable of dissolving the oxidation product, and decomposing the reaction product with an acid.

Oxidation of TIPB yields, besides the objective product THPO and the above-mentioned carbinol compounds, various by-products represented by the above formula (I) including dihydroperoxide ($A_1$:—H; $A_2$ and $A_3$:—OOH), monohydroperoxide ($A_1$ and $A_2$:—H; $A_3$:—OOH), monocarbinol monohydroperoxide ($A_1$:—H; $A_2$:—OH; $A_3$:—OOH), dicarbinol ($A_1$:—H; $A_2$ and $A_3$:—OH), and monocarbinol ($A_1$ and $A_2$:—H; and $A_3$:—OH), of TIPB.

Starting materials available in this invention include various states of oxidation product of TIPB containing said carbinol compounds, such as an oxidation product itself, an oxidation product containing carbinol compound removing part of by-products other than TIPB and/or the carbinol compounds, an oxidation product removing as much as possible, by-products other than the carbinol compounds, and the like. However, because there are great differences of reactivity to hydrogen peroxide between the carbinol compounds and other by-products such as monocarbinol monohydroperoxide and dicarbinol, it is undesirable to react these compounds under the same condition, in view of adverse effects on the yield, consumption, of hydrogen peroxide, after treatments such as separation and purification, etc. Accordingly, it is most desirable in this invention to use products, as the starting material, obtained by previously removing by-products other than the carbinol compounds from the product mixture obtained by oxidation of TIPB, for instance, by extraction with an aqueous alkali solution or recrystallization. Preferably, the by-products other than the carbinol compounds are removed, in this case, until their content in the starting material reduces to 30% by weight or less.

Carbinol compounds isolated from the oxidation product mixture can also be used as the starting material in this invention.

Hydrogen peroxide is best used in the form of aqueous solution, though it is possible to apply hydrogen peroxide-generating materials such as sodium peroxide, calcium peroxide, etc.

The amounts of hydrogen peroxide used are 1.5 to 10 equivalents, preferably 2 to 6 equivalents based on carbinol group contained in the oxidation reaction product, where excess hydrogen peroxide can be recycled. The concentrations of the aqueous hydrogen peroxide are generally 5 to 50%, preferably 10 to 40%, by weight.

The reaction between hydrogen peroxide and the oxidation reaction product of TIPB, in this invention, is carried out in a heterogeneous system in the presence of an acid catalyst and a solvent inert to hydrogen peroxide and capable of dissolving the oxidation reaction product.

Acid catalysts suitable for this reaction include sulfuric acid, perchloric acid, hydrochloric acid, phosphoric acid, p-toluenesulfonic acid, and chloroacetic acid, of which sulfuric acid, perchloric acid, and phosphoric acid are preferred in particular.

Suitable amounts of these acid catalysts herein, though dependent on the kind of acid, are generally within the range of 0.05 to 0.5 mol/l in terms of concentration in the aqueous hydrogen peroxide. The amount of acid catalyst has a significant effect on the yield, that is, too large amounts of acid catalyst, though effective for increasing the reaction rate, deteriorate the stability of the objective product, THPO, and this results in decreased yields of THPO and consequently reduces the yield of phloroglucin in the subsequent decomposition reaction. On the other hand, too small amounts of acid catalyst bring about insufficient conversions of the carbinol compounds and consequent low yield of THPO, and naturally the carbinol compounds remaining in the reaction product result in decreased yield of phloroglucin in the next decomposition step.

Whereas very large amounts of acid catalyst are necessary for the production of monovalent or divalent phenols, a very small amount thereof is effective for the production of phloroglucin as stated above. This fact was found out for the first time by the present inventors and is a feature of this invention.

Solvents applicable to this first step reaction are organic solvents inert to hydrogen peroxide and capable of dissolving the starting material, namely, the above-mentioned oxidation product and include halogenated hydrocarbons and ethers, for example, dichloroethane, monochlorobenzene, o-dichlorobenzene, trichloroethane, tetrachloroethane, chlorobromomethane, isopropyl ether, and n-butyl ether, of which dichloroethane, monochlorobenzene, and isopropyl ether are preferable.

Aliphatic and aromatic hydrocarbons as a solvent are undesirable for this reaction, since they do not thoroughly dissolve the oxidation reaction product, forming a dispersion thereof in the solvent and this causes a decrease in the yield of the objective THPO and unsatisfactory separation of the organic solvent layer from the aqueous hydrogen peroxide solution layer after completion of the reaction. Ketones, alcohols, and esters are also undesirable, since they are reactive to hydrogen peroxide, the use of such a solvent results in an increased consumption of hydrogen peroxide and formation of by-products. When the oxidation reaction product is reacted with hydrogen peroxide without any organic solvent, the oil layer becomes highly viscous, much carbinol compounds remain unreacted, thus not only lowering the yield of THPO but also allowing the separation of the oil layer from the aqueous layer after compeltion of the reaction to make difficult.

When the organic solvent specified in this invention is used, the oxidation reaction product of TIPB completely dissolves therein and is brought into an ideal heterogeneous state for contacting with the aqueous hydrogen peroxide, whereby almost no carbinol compound is left unreacted and therefore THPO, the intermediate for producing phloroglucin in the present process, can be obtained in a high yield. In addition, the use of the specified solvent simplifies the separation of the aqueous hydrogen peroxide layer and the THPO-containing organic solvent layer, so that the separated excess hydrogen peroxide can be effectively recycled with ease.

Suitable amounts of the solvent used, though dependent upon the kind of solvent and conditions of the reaction, are generally in the range of 0.5 to 10 times the weight of the oxidation reaction product.

Desirable temperatures of the reaction of the oxidation reaction product with the aqueous hydrogen peroxide are high enough for the solvent to dissolve the oxidation reaction product completely, usually ranging from 40° to 70° C.

The reaction of the oxidation reaction product of TIPB with hydrogen peroxide can be carried out either batchwise or continuously, the mode of the reaction itself being under no particular restriction. The water produced by the reaction can be removed by azeotropic distillation during or after the reaction or by distillation of the aqueous layer separated from the oil layer after completion of the reaction.

THPO thus obtained by reacting the carbinol compounds in the oxidation reaction product with hydrogen peroxide is then decomposed in usual manner by contacting with an acid catalyst immediately or, if necessary, after removal of acid catalyst used in the preceding reaction and water or after further removal of part or all of the solvent from THPO and addition of some other solvent.

After the decomposition, phloroglucin of high purity can be obtained from the reaction mixture, for instance, by distillation to remove the solvent, extraction, and recrystallization.

This invention will be illustrated in more detail with reference to the following Examples, wherein "parts" and "%" are by weight.

REFERENCE EXAMPLE 1

(1) TIPB was oxidized by blowing oxygen gas into a mixture of 100 parts of TIPB and 100 parts of water at 95°–100° C. for 72 hours with stirring while keeping the pH of the reaction mixture at 9–10 by addition of aqueous sodium hydroxide solution. The oxidation reaction product was obtained as an oily matter by separating the resulting reaction mixture.

The composition of the oily matter was as follows: 13.7 wt. % of THPO, 17.8 wt. % of carbinol dihydroperoxide, 2.5 wt. % of dicarbinol hydroperoxide, 0.5 wt. % of tricarbinol, 24.6 wt. % of 1,3,5-triisopropylbenzene dihydroperoxide, 13.9 wt. % of carbinol hydroperoxide, 1.4 wt. % of dicarbinol, 9.8 wt. % of 1,3,5-triisopropylbenzene monohydroperoxide, 1.0 wt. % of TIPB, and 14.8 wt. % of the remainder.

(2) An aqueous alkali solution was added to the oxidation reaction product obtained, and the resulting oil and aqueous layers were separated. The aqueous alkali layer was neutralized and extracted with dichloroethane, to obtain a dichloroethane solution of oxidation reaction product having the following composition:

7.9 parts of THPO, 9.3 parts of carbinol dihydroperoxide, 1.7 parts of dicarbinol hydroperoxide, 0.1 part of tricarbinol, 0.2 part of 1,3,5-triisopropylbenzene dihydroperoxide, 78.0 parts of dichloroethane, and 2.8 parts of the remainder.

EXAMPLE 1

(1) The dichloroethane solution (100 parts) of oxidation reaction product prepared in Reference Example 1 was reacted with 39.5 parts of an aqueous solution containing 20% of hydrogen peroxide (amount of hydrogen peroxide: 5 equivalents based on carbinol group) and 1.0% of sulfuric acid with stirring at 60°–63° C. for 4 hours. The resulting oil layer was isolated, neutralized, and washed with water, to obtain a reaction product consisting of 16.6 wt. % of THPO and 83.4 wt. % of dichloroethane and the like. This reaction product contained almost no carbinol compound and the yield of THPO was 84.2% based on the total amount of THPO and carbinol compounds present in the oxidation product used.

The aqueous layer separated from the oil layer contained 16.6% of hydrogen peroxide and 0.98% of sulfuric acid.

(2) Methyl isobutyl ketone was added to the above produced dichloroethane solution, and the mixture was concentrated and dehydrated to give a methyl isobutyl ketone solution of THPO. This solution (100 parts) was added dropwise to a mixture of 0.00075 part of perchloric acid and 25 parts of actone at 56°-60° C. to decompose the THPO into 5.6 parts of phloroglucin.

A moment at which the hydroperoxide concentration in the reaction mixture measured by iodometry became to 0.1% was regarded as the end point of the decomposition reaction. The yield of phloroglucin was 80.4% based on THPO used.

EXAMPLE 2

TIPB was oxidized in the same manner as in Reference Example 1 except for using chlorobenzene in place of dichloroethane as a solvent for extracting the oxidation product. The oxidation reaction product dissolved in chlorobenzene was reacted with hydrogen peroxide in the same manner as in Example 1 (1).

The oil layer obtained in this reaction contained almost no carbinol compound and the yield of THPO was 80.5% based on the total amount of THPO and carbinol compounds present in the oxidation product used.

EXAMPLE 3

A n-butyl ether solution of oxidation reaction product of TIPB was obtained in the same manner as in Reference Example 1 except for using n-butyl ether in place of dichloroethane as a solvent for extracting the oxidation product. The solution of oxidation product was reacted with hydrogen peroxide in the same manner as in Example 1. The oil layer obtained in this reaction contained almost no carbinol compound and the yield of THPO was 78.0% based on the total amount of THPO and carbinol compounds present in the oxidation reaction product used.

EXAMPLE 4

The oxidation reaction product (100 parts) obtained in Reference Example 1 (1) (the treatment of Reference Example 1 (2) was not applied thereto) was dissolved in 400 parts of dichloroethane and reacted with 124.8 parts of a solution containing 20% of hydrogen peroxide and 1.0% of sulfuric acid (amount of hydrogen peroxide: 5 equivalents based on carbinol group) at 60°-63° C. for 4 hours with stirring.

The composition of the oil layer obtained was as follows: 5.5 wt. % of THPO, 0.2 wt. % of carbinol dihydroperoxide, 4.7 wt. % of 1,3,5-triisopropylbenzene dihydroperoxide, 1.3 wt. % of monocarbinol monohydroperoxide, 0.1 part of dicarbinol, and 88.2 wt. % of the remainder.

The yield of THPO was 80.1% based on the total amount of THPO and carbinol compounds present in the oxidation product used.

EXAMPLE 5

An aqueous solution containing 20% of hydrogen peroxide and 1.0% of sulfuric acid was prepared by adding hydrogen peroxide and sulfuric acid to the aqueous layer recovered in Example 1 (1).

This aqueous hydrogen peroxide solution (39.5 parts) was reacted with 100 parts of the dichloroethane solution of oxidation reaction product obtained in Reference Example 1, in the same manner as in Example 1 (1). The resulting oil layer and aqueous hydrogen peroxide solution layer were separated.

Using the aqueous hydrogen peroxide solution thus recovered, the reaction with the oxidation reaction product was carried out in the same manner as mentioned above. Thus, the aqueous hydrogen peroxide solution was recycled five times. The oil layer obtained in each reaction consisted of 16.4-16.8 wt. % of THPO and 83.6-83.2 wt. % of the remainder. Each aqueous layer for the recycling contained 16.5-16.8 wt. % of hydrogen peroxide and 1.0-0.97 wt. % of sulfuric acid after completion of each preceding reaction.

The yield of THPO in each reaction was 83-85% based on the total amount of THPO and carbinol compounds present in the oxidation reaction product used.

COMPARATIVE EXAMPLE 1

The oil layer (100 parts; oxidation reaction product of TIPB) obtained in the method of Reference Example 1 (1) was reacted with 124.8 parts of an aqueous solution containing 20.0% of hydrogen peroxide and 1.0% of sulfuric acid (amount of hydrogen peroxide: 5 equivalents based on carbinol group) at 60°-63° C. for 4 hours with stirring. During the reaction, the oil layer became a highly viscous mass, which made the oil and water layer separation extremely difficult after completion of the reaction.

The composition of the oil layer was as follows: 21.3 wt. % of THPO, 5.8 wt. % of carbinol dihydroperoxide, 23.6 wt. % of 1,3,5-triisopropylbenzene dihydroperoxide, 6.6 wt. % of monocarbinol monohydroperoxide, 0.6 wt. % of dicarbinol, and 42.1 wt. % of the remainder.

The yield of THPO was 62.0% based on the total amount of THPO and carbinol compounds present in the oxidation product used.

The concentration of hydrogen peroxide in the recovered aqueous layer was 16.3 wt. %.

COMPARATIVE EXAMPLE 2

A toluene solution of oxidation product of TIPB was obtained in the same manner as in Reference Example 1 except for using toluene in place of dichloroethane as the solvent. This solution was reacted with hydrogen peroxide in the same manner as in Example 1 (1). During the reaction, the reaction mixture was in a state such that solid matter is dispersed in oil layer of the reaction mixture and the oil and water layer separation after completion of the reaction was unfavorable.

The composition of the oil layer obtained was as follows: 13.3 wt. % of THPO, 3.5 wt. % of carbinol dihydroperoxide, and 83.2 wt. % of the remainder. The yield of THPO was 67.4% based on the total amount of THPO and carbinol compounds present in the oxidation product used.

COMPARATIVE EXAMPLE 3

A methyl isobutyl ketone solution of oxidation reaction product of TIPB was obtained in the same manner as in Reference Example 1 except for using methyl isobutyl ketone in place of dichloroethane as the solvent. This solution was reacted with hydrogen peroxide in the same manner as in Example 1 (1).

The composition of the oil layer after completion of the reaction was as follows: 12.3 wt. % of THPO, 5.9 wt. % of carbinol dihydroperoxide, and 81.8 wt. % of the remainder. The concentration of hydrogen peroxide in the aqueous layer was 14.1 wt. %.

What is claimed is:

1. A process for producing phloroglucin which comprises reacting an oxidation product containing at least one carbinol compound of carbinol dihydroperoxide, dicarbinol hydroperoxide and tricarbinol obtained by oxidation of 1,3,5-triisopropylbenzene, with hydrogen peroxide in a heterogeneous system in the presence of an acid catalyst and an organic solvent inert to the hydrogen peroxide and capable of dissolving the oxidation product, and thereafter decomposing the reaction product with an acid, wherein the organic solvent is a halogenated hydrocarbon or ether, wherein the amount of hydrogen peroxide is in the range of 1.5 to 10 equivalents based on carbinol group of the carbinol compounds, and wherein the hydrogen peroxide is used in an aqueous solution having a concentration of 5 to 50% by weight.

2. The process for producing phloroglucin according to claim 1, wherein the acid catalyst is sulfuric acid, phosphoric acid or perchloric acid.

3. The process for producing phloroglucin according to claim 1, wherein the concentration of acid catalyst is 0.05 to 0.5 mol/l based on the aqueous solution of hydrogen peroxide.